(12) United States Patent
Ajiki et al.

(10) Patent No.: US 9,775,986 B2
(45) Date of Patent: Oct. 3, 2017

(54) TEETH SURFACE STAIN REMOVING APPARATUS AND TEETH SURFACE STAIN REMOVING METHOD

(71) Applicant: Panasonic Intellectual Property Management Co., Ltd., Osaka (JP)

(72) Inventors: Kaori Ajiki, Osaka (JP); Risa Otsuka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/860,141

(22) Filed: Sep. 21, 2015

(65) Prior Publication Data
US 2016/0096014 A1 Apr. 7, 2016

(30) Foreign Application Priority Data
Oct. 3, 2014 (JP) ................. 2014-205078

(51) Int. Cl.
*A61C 3/00* (2006.01)
*A61C 19/00* (2006.01)
(Continued)

(52) U.S. Cl.
CPC .......... *A61N 1/0548* (2013.01); *A61C 19/066* (2013.01); *A61N 1/0492* (2013.01); *A61N 1/205* (2013.01)

(58) Field of Classification Search
CPC ... A61C 19/066; A61C 1/0007; A61C 1/0015; A61N 1/0548; A61N 1/0492;
(Continued)

(56) References Cited

U.S. PATENT DOCUMENTS

2005/0202363 A1* 9/2005 Osterwalder ........ A61C 9/0006
433/29
2006/0234189 A1* 10/2006 Duret .................. A61C 19/066
433/215
(Continued)

FOREIGN PATENT DOCUMENTS

AU   2006202776   8/2006
EP   1525857      4/2005
(Continued)

OTHER PUBLICATIONS

Satoshi Aihara et al. "Trend in Research on Organic Imaging Devices" NHK Science & Technology Research Laboratories R&D No. 132, pp. 4-11, Mar. 2012.

(Continued)

*Primary Examiner* — Yogesh Patel
*Assistant Examiner* — Gwen M Demosky
(74) *Attorney, Agent, or Firm* — Greenblum & Bernstein, P.L.C.

(57) ABSTRACT

A teeth surface stain removing apparatus removes stains on a teeth surface, and includes a sheet member capable of being attached to the teeth surface via an adsorptive member for adsorbing the stains, a teeth surface electrode disposed at a part of the sheet member, the part being attached to the teeth surface, and a charge supplier supplying negative charges to the teeth surface electrode in a state where the sheet member is attached to the teeth surface.

20 Claims, 8 Drawing Sheets

(51) Int. Cl.
*A61N 1/05* (2006.01)
*A61C 19/06* (2006.01)
*A61N 1/04* (2006.01)
*A61N 1/20* (2006.01)

(58) Field of Classification Search
CPC ...... A61N 1/205; A61N 1/048; A61N 1/0404; A61N 1/04; A61N 1/18
USPC ........ 433/6, 29, 32, 37, 41–48, 80, 215–216
See application file for complete search history.

(56) References Cited

U.S. PATENT DOCUMENTS

| | | | |
|---|---|---|---|
| 2007/0276455 A1* | 11/2007 | Fiset | A61C 19/066 607/91 |
| 2008/0060148 A1* | 3/2008 | Pinyayev | A61B 5/0088 15/22.1 |
| 2008/0086189 A1 | 4/2008 | Taniguchi et al. | |
| 2008/0199830 A1* | 8/2008 | Fontenot | A46B 5/0012 433/215 |
| 2008/0233541 A1 | 9/2008 | De Vreese et al. | |
| 2009/0058274 A1 | 3/2009 | Yokoyama et al. | |
| 2012/0251971 A1* | 10/2012 | Fish | A46B 15/0002 433/27 |
| 2012/0315596 A1* | 12/2012 | Gan | A61C 19/066 433/32 |
| 2013/0040264 A1* | 2/2013 | Scurtescu | A61C 1/07 433/119 |
| 2013/0164701 A1* | 6/2013 | Inglese | G01J 3/02 433/29 |
| 2015/0044628 A1* | 2/2015 | Flyash | A61C 19/066 433/27 |

FOREIGN PATENT DOCUMENTS

| | | |
|---|---|---|
| FR | 2873297 | 1/2006 |
| JP | 2001-181163 | 7/2001 |
| JP | 2008-093038 | 4/2008 |
| JP | 2009-048837 | 3/2009 |
| JP | 2009-120742 | 6/2009 |
| JP | 2012-005659 | 1/2012 |
| JP | 2012-110500 | 6/2012 |
| JP | 2013-168575 | 8/2013 |

OTHER PUBLICATIONS

The Extended European Search Report dated Mar. 2, 2016 for the related European Patent Application No. 15186181.2.

* cited by examiner

| BLOCK | COLOR-TONE SENSOR UNIT | TEETH SURFACE ELECTRODE UNIT |
|---|---|---|
| FIRST BLOCK | FIRST AND SECOND COLOR-TONE SENSOR UNITS | FIRST TO FOURTH TEETH SURFACE ELECTRODE UNITS |
| SECOND BLOCK | THIRD AND FOURTH COLOR-TONE SENSOR UNITS | FIFTH TO EIGHTH TEETH SURFACE ELECTRODE UNITS |
| ⋮ | ⋮ | ⋮ |
| Lth BLOCK | ⋯Mth COLOR-TONE SENSOR UNIT | ⋯Nth TEETH SURFACE ELECTRODE UNIT |

| COLOR-TONE LEVEL ~721 | CURRENT VALUE ~722 | ENERGIZING TIME ~723 |
|---|---|---|
| C0 | 0 | 0 |
| C1 | I1 | T1 |
| C2 | I2 | T2 |
| ⋮ | ⋮ | ⋮ |

TEETH SURFACE STAIN REMOVING APPARATUS AND TEETH SURFACE STAIN REMOVING METHOD

BACKGROUND OF THE INVENTION

1. Field of the Invention

The present disclosure relates to a teeth surface stain removing apparatus and a teeth surface stain removing method.

2. Description of the Related Art

The surface of teeth is coated with a thin film of saliva called a pellicle. When components such as calcium ($Ca^{2+}$) and metal ions contained in the pellicle, and components such as tannins contained in coffee and the like and proteins including albumin in the oral cavity are bonded to each other, discoloring matter, which is referred to as stains, appears on the surface of teeth (hereinafter referred to as the "teeth surface").

Conventionally, there exists a technique of removing stains on the teeth surface using minor current (for example, see Patent Literatures 1 and 2). According to the technique disclosed in Patent Literatures 1 and 2 (hereinafter referred to as the "conventional technique"), an electrode is disposed at each of the head portion and the grip portion of a toothbrush or a toothbrush-like member, and current is passed such that negative ions are supplied to the teeth surface. By being supplied with negative ions, stains become less likely to be fixed on the teeth surface. Therefore, according to the conventional technique, stains can be efficiently removed by brushing of the teeth.

CITATION LIST

Patent Literatures

PTL 1: Unexamined Japanese Patent Publication No. 2008-93038
PTL 2: Unexamined Japanese Patent Publication No. 2012-5659
PTL 3: Unexamined Japanese Patent Publication No. 2013-168575
PTL 4: Unexamined Japanese Patent Publication No. 2009-120742
PTL 5: Unexamined Japanese Patent Publication No. 2009-48837
PTL 6: Unexamined Japanese Patent Publication No. 2008-93038
PTL 7: Unexamined Japanese Patent Publication No. 2001-181163

Non-Patent Literature

NPL 1: Satoshi Aihara, Misao Kubota, "Trend in research on organic imaging devices", NHK Science and Technology Research Laboratories R&D No. 132, NHK Science and Technology Research Laboratories, March 2012, PP. 4-11

However, it is difficult to apply the conventional technique to people having difficulty in brushing teeth; such as bedridden elderly patients. Further, in order to fully attain the stain removing effect, it is required to brush teeth for a certain time period. However, in some cases, it may be difficult to take such time. Accordingly, a technique that makes it possible to remove stains on the teeth surface more easily is desired.

SUMMARY

Thus, a non-limiting exemplary embodiment of the present disclosure provides a teeth surface stain removing apparatus and a teeth surface stain removing method which make it possible to remove stains more easily.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: a teeth surface stain removing apparatus, the apparatus including: a sheet member attachable to a teeth surface via an adsorptive member for adsorbing stains: a teeth surface electrode disposed at a part of the sheet member, the part being attached to the teeth surface; and a charge supplier supplying negative charges to the teeth surface electrode in a state where the sheet member is attached to the teeth surface.

These general and specific aspects may be implemented using a device, a system, a method, a sheet, and a computer program, and any combination of devices, systems, methods, sheets, and computer programs.

According to the present disclosure, stains can be removed more easily.

DETAILED DESCRIPTION

In the following, exemplary embodiments of the present disclosure will be described in detail with reference to the drawings.

First Exemplary Embodiment

A first exemplary embodiment of the present disclosure is one example of a basic embodiment of the present disclosure.

Figure 1:
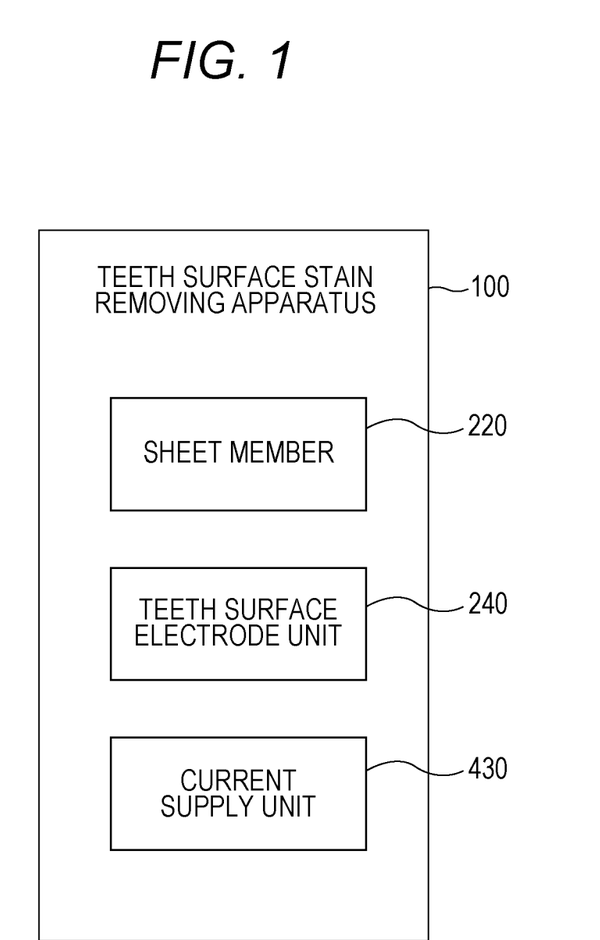
FIG. 1 shows one example of the structure of a teeth surface stain removing apparatus according to a first exemplary embodiment.

FIG. 1 is a block diagram showing one example of the structure of a teeth surface stain removing apparatus according to the present exemplary embodiment.

In FIG. 1, teeth surface stain removing apparatus 100 is an apparatus that removes stains on the teeth surface, and includes sheet member 220, teeth surface electrode unit 240, and charge supplying unit 430.

Sheet member 220 is a sheet-like member that can be closely attached to the teeth surface via an adsorptive member that adsorbs stains.

Tooth surface electrode unit 240 is an electrode unit disposed at a part of sheet member 220, the part being closely attached to the teeth surface.

Charge supplying unit 430 supplies negative charges to teeth surface electrode unit 240, in the state where sheet member 220 is closely attached to the teeth surface.

Note that, although not shown, teeth surface stain removing apparatus 100 includes a power supply unit, such as a storage battery or a commercial power supply connection unit. In this case, the charge supplying unit 430 includes a circuit that controls the electrical connection state between the power supply unit and teeth surface electrode unit 240.

Tooth surface stain removing apparatus 100 structured as described above makes it possible to remove stains more easily.

Second Exemplary Embodiment

A second exemplary embodiment of the present disclosure is an example of a specific embodiment in the case where the present disclosure is applied to a sheet that can be attached to the entire teeth surface on the lip side of the upper anterior teeth.

Appearance and Structure of Teeth Surface Stain Removing Apparatus

Firstly, a description will be given of the appearance and structure of the teeth surface stain removing apparatus according to the present exemplary embodiment.

Appearance of Teeth Surface Stain Removing Apparatus

Figure 2:
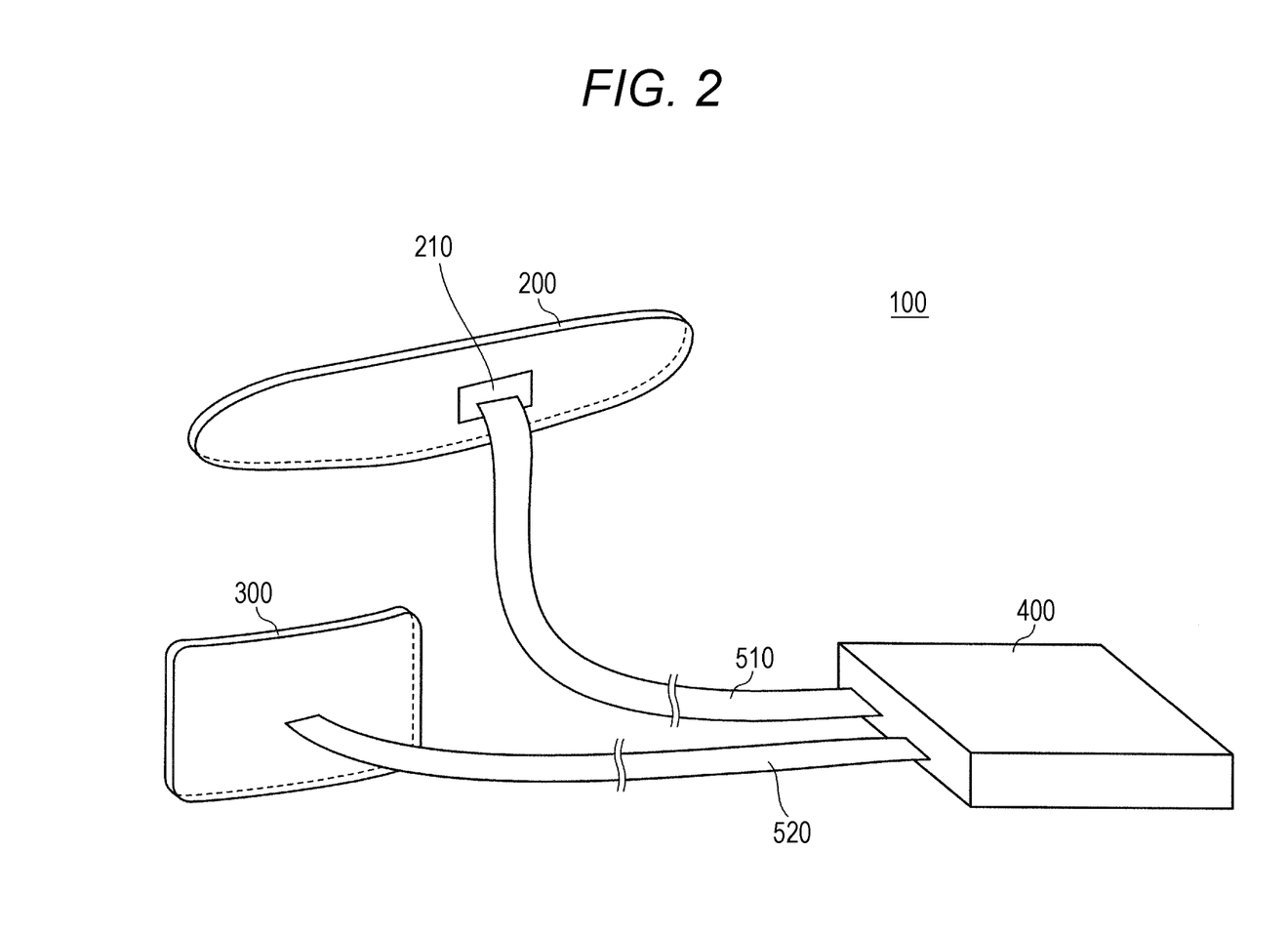
FIG. 2 shows one example of the appearance of a teeth surface stain removing apparatus according to a second exemplary embodiment.

FIG. 2 is a diagram showing one example of the appearance of the teeth surface stain removing apparatus according to the present exemplary embodiment.

As shown in FIG. 2, teeth surface stain removing apparatus 100 includes first sheet device 200, second sheet device 300, and control unit 400.

Figure 3:
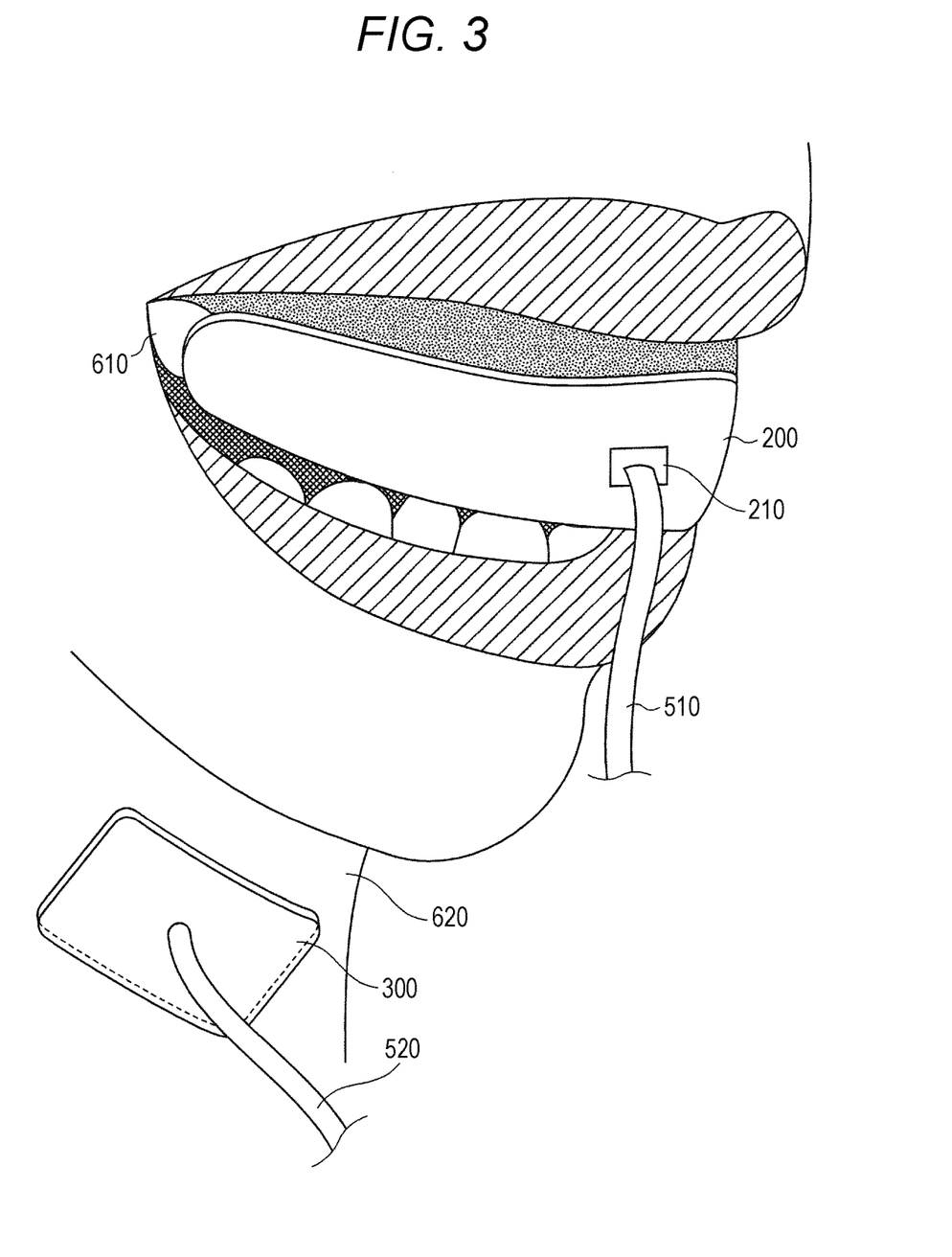
FIG. 3 shows one example of the state where the teeth surface stain removing apparatus according to the second exemplary embodiment is attached.

First sheet device 200 is a member attached to the teeth surface of a user. Second sheet device 300 is a member attached to any body site other than the teeth surface of a user, e.g., the skin of the neck or an arm. FIG. 3 is a diagram showing an example of the state where first sheet device 200 and second sheet device 300 are attached.

First sheet device 200 is a sheet-like device being large enough to cover the entire teeth surface on the lip side of the upper anterior teeth (hereinafter referred to as the "anterior teeth portion") 610. The base member of first sheet device 200 is a sheet member being elastic and flexible, and first sheet device 200 can be closely attached to the teeth surface by being deformed conforming to the three-dimensional shape of the teeth surface. Note that, in the present exemplary embodiment, being closely attached is not limited to being totally closely attached over the entire surface, and includes the state being partially closely attached, for example with sparse clearances between the two surfaces.

An example of the sheet member of first sheet device 200 may include a cured energy ray-curable composition containing acryloyl group-terminated urethane polymer and acrylic monomer (for example, see Patent Literature 3).

First sheet device 200 includes, on the side attached to anterior teeth portion 610 (hereinafter referred to as the "teeth surface side"), a layer made of a predetermined adsorptive member that adsorbs stains removed from the teeth surface. That is, an adsorptive member is carried on the teeth surface side of the sheet member being the base member. The adsorptive member is a material having predetermined electrical conductivity, light-transmittance, biocompatibility, resilience, and adhesiveness. First sheet device 200 is capable of maintaining the state being closely attached to the teeth surface by the adhesiveness of the adsorptive member.

Examples of the material of the adsorptive member of first sheet device 200 may include perfluorosulfonic acid copolymer, perfluorocarboxylic acid copolymer, polystyrene sulfonic acid copolymer, polystyrene carboxylic acid copolymer, or PEDOT-PSS{poly(3,4-ethylenedioxythiophene)-poly(styrenesulfonate)}. Further, an example of the structure of the adsorptive member of first sheet device 200 may include a foamed structure on the surface of which a fine foamed body exhibiting a suction function is formed (for example, see Patent Literature 4).

On the teeth surface side of the sheet member of first sheet device 200, a plurality of color-tone sensor units and a plurality of teeth surface electrode units (both not shown and collectively referred to as the "element group" as appropriate) are disposed.

The electrode surface of each teeth surface electrode unit is disposed on the teeth surface side of the sheet member, and in contact with the adsorptive member which is fully electrically conductive. Although a description will be given later, the teeth surface electrode units are supplied with negative charges from control unit 400. That is, the teeth surface electrode units supply negative ions to stains on the teeth surface, in the state where first sheet device 200 is attached to the teeth surface.

Note that, desirably the size of first sheet device 200 can be selected from a plurality of types, in accordance with the variations in size of anterior teeth portion 610.

Second sheet device 300 is a sheet-like device having a similar size as first sheet device 200, and the base member of second sheet device 300 is a sheet member similar to that of first sheet device 200.

Second sheet device 300 includes a layer made of a predetermined adhesive member on the side attached to body part 620 (hereinafter referred to as the "skin side"). The adhesive member is a material having predetermined electrical conductivity, biocompatibility, resilience, and adhesiveness. Second sheet device 300 can maintain the state closely attached to the skin, by the surface tension or adhesiveness of the adhesive member.

Examples of the adhesive member of second sheet device 300 may include Spirit Gum, a silicone adhesive, a latex adhesive, and the like.

Further, on the skin side of the sheet member of second sheet device 300, a skin electrode unit (not shown) is disposed.

The electrode surface of the skin electrode unit is disposed on the skin side of the sheet member, and in contact with the adhesive member which is fully electrically conductive. Although a description will be given later, the skin electrode unit is supplied with positive charges from control unit 400. That is, the skin electrode unit supplies positive charges to the skin, in the state where second sheet device 300 is attached to the skin.

Control unit 400 is an apparatus unit protected by a housing made of a material such as plastic. Control unit 400 has a function of controlling the element group of first sheet device 200 and the operation of the skin electrode unit of second sheet device 300. In particular, control unit 400 applies voltage across the teeth surface electrode units of first sheet device 200 and the skin electrode unit of the second sheet device, to supply negative charges to the teeth surface electrode units and to supply positive charges to the skin electrode unit. Control unit 400 is connected to first sheet device 200 and second sheet device 300 via first and second cables 510 and 520.

Although not shown, first cable 510 includes a signal line connecting between control unit 400 and the element group of first sheet device 200. Although not shown, second cable 520 includes a signal line connecting between control unit 400 and the skin electrode unit of second sheet device 300. Note that, first and second cables 510 and 520 desirably have a length that allows control unit 400 to be stored in a pocket of the clothing of the user, for example in the state where first sheet device 200 and second sheet device 300 are attached to the teeth and the neck, respectively.

Note that, first sheet device 200 includes connection unit 210 that disconnectably connects between first sheet device 200 and first cable 510. Connection unit 210 is a small modular jack, which, for example, includes therein a nail fitting portion and a contact portion for the signal line. First sheet device 200 is a disposable member that can be removed from control unit 400 and replaced with a new piece, every time adsorption of stains ends.

Structure of Sheet Device

Figure 4:
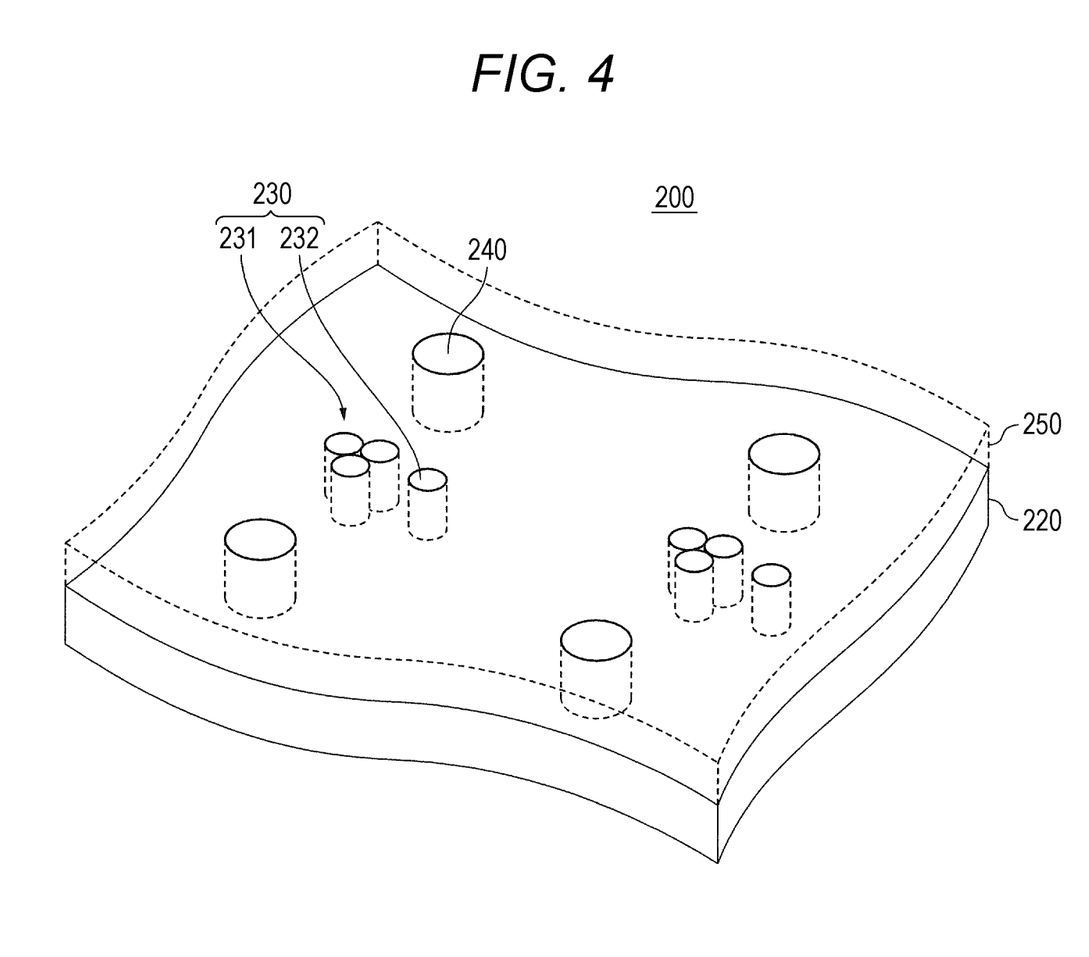
FIG. 4 shows one example of the structure of a first sheet device according to the second exemplary embodiment.

FIG. 4 is a block diagram showing one example of the structure of first sheet device 200. Note that, only the representative part out of the entire first sheet device 200 is shown herein.

In FIG. 4, first sheet device 200 has a structure in which color-tone sensor units 230 and teeth surface electrode units 240 are embedded in sheet member 220.

Each color-tone sensor unit 230 includes light emitting element 231 outputting white-color light, and color-tone sensor 232 receiving the light output from light emitting element 231 and reflected off the teeth surface. The light emitting surface of light emitting element 231 and the light receiving surface of color-tone sensor 232 are disposed on the surface of sheet member 220 on the teeth surface side.

Adsorptive member 250 is layered on the surface of sheet member 220 on the teeth surface side. The adsorptive member fully transmits light. Further, by the thickness of the adsorptive member, color-tone sensor 232 is disposed such that the light receiving surface is spaced apart from the teeth surface by about 100 micrometers, for example in the state where first sheet device 200 is closely attached to the teeth surface. That is, each color-tone sensor unit 230 detects the color tone of the nearby teeth surface, in the state where first sheet device 200 is attached to the anterior teeth portion.

As described above, the electrode surface of each teeth surface electrode unit 240 is in contact with adsorptive member 250, and supplied with negative charges from control unit 400 (see FIG. 2). Adsorptive member 250 has a thickness and electrical conductivity which cause, when current of a predetermined level is output from the electrode surface of each teeth surface electrode unit 240, charges to be supplied only to the region near the electrode surface, in the teeth surface being in contact with adsorptive member 250. Accordingly, teeth surface electrode unit 240 supplies negative charges to the nearby teeth surface, in the state where first sheet device 200 is attached to the anterior teeth portion.

Stains attached to the teeth surface become easier to be removed from the teeth surface by being supplied with negative ions. The stains becoming easier to be removed are adsorbed by adsorptive member 250 of first sheet device 200. Then, by first sheet device 200 including adsorptive member 250 being peeled off from the teeth surface, the stains on the teeth surface are removed from the teeth surface.

Note that, desirably color-tone sensor units 230 and teeth surface electrode units 240 are small as much as possible.

An example of color-Mane sensor 232 of a small size may include a device that can capture three primary colors of R, G, and B by an organic semiconductor, as disclosed in Non-Patent Literature 1. The color-tone sensor disclosed in Non-Patent Literature 1 is capable of being finely formed by printing.

An example of light emitting element 231 of a small size may include an organic LED element formed by printing using polymer, as disclosed in Patent Literature 5.

Teeth surface electrode unit 240 may be made of a Co—Cr-base alloy, for example.

Measure of Control of Sheet Device

In the present exemplary embodiment, the operation of first sheet device 200 is controlled by a region-by-region basis. The regions are obtained by dividing first sheet device 200 into a plurality of small regions each having a side of about several millimeters. In the following, each division region of first sheet device 200 and a measure of control is referred to as a "block".

In one block, it is assumed at least one color-tone sensor unit 230 and at least one teeth surface electrode unit 240 are disposed. The arrangement density of color-tone sensor units 230 and teeth surface electrode units 240 may be uniform in first sheet device 200. Alternatively, the density may vary among the blocks, or within a block.

In the present exemplary embodiment, it is assumed that L-pieces of blocks are set in first sheet device 200. Then, a plurality of color-tone sensor units 230 and a plurality of teeth surface electrode units 240 belong to one block. Further, the area is substantially identical among the L-pieces of blocks. Further, the arrangement density of color-tone sensor units 230 and teeth surface electrode units 240 is also substantially identical among the L-pieces of blocks.

Functional Structure of Teeth Surface Stain Removing Apparatus

Figure 5:
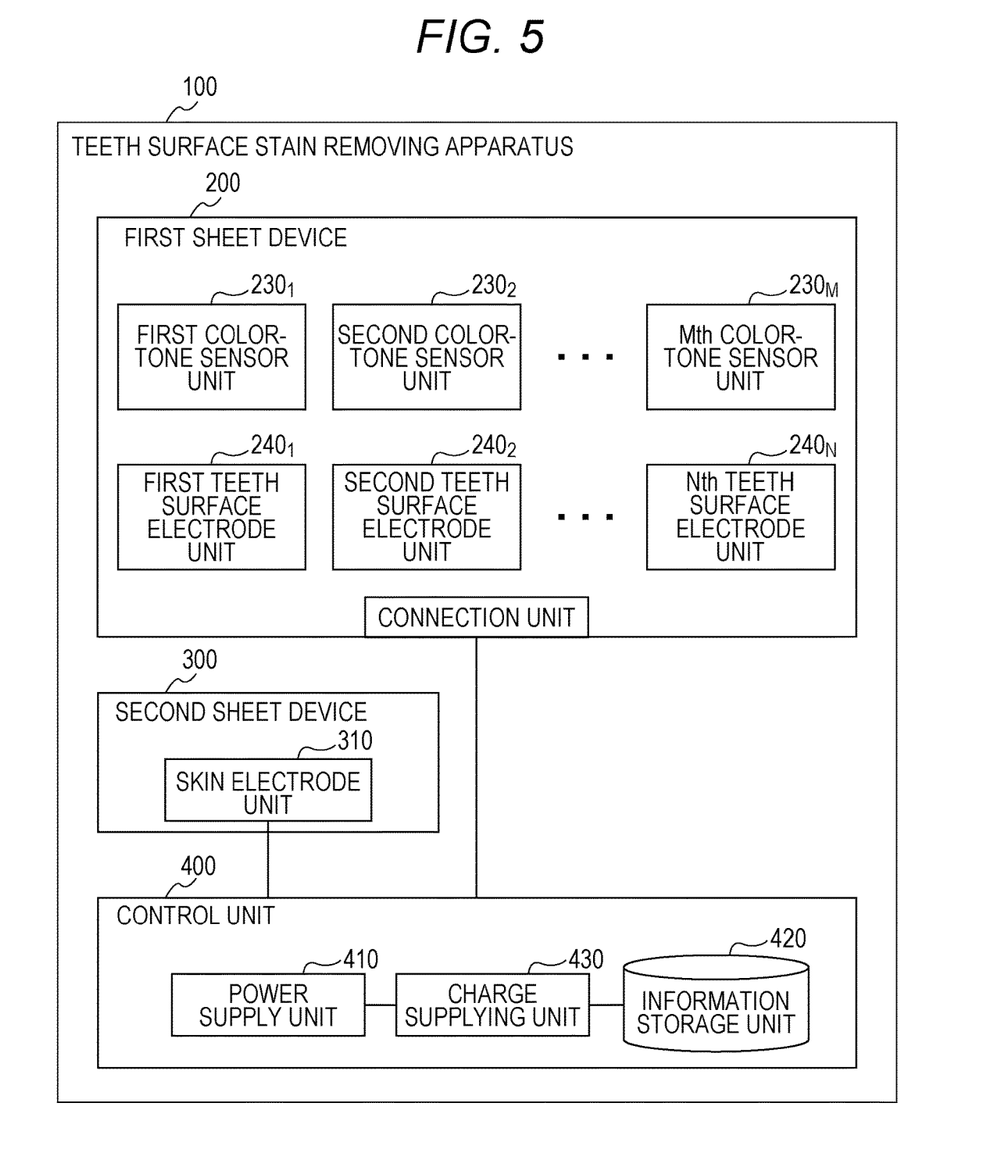
FIG. 5 shows one example of the structure of the teeth surface stain removing apparatus according to the second exemplary embodiment.

FIG. 5 is a diagram showing one example of the functional structure of teeth surface stain removing apparatus 100.

In FIG. 6, teeth surface stain removing apparatus 100 includes first to Mth color-tone sensor units $230_1$ to $230_M$ and first to Nth teeth surface electrode units $240_1$ to $240_N$ disposed at first sheet device 200. Further, teeth surface stain removing apparatus 100 includes skin electrode unit 310 disposed at second sheet device 300, and power supply unit 410, information storage unit 420, and charge supplying unit 430 disposed at control unit 400.

Power supply unit 410 is a storage battery, a commercial power supply connection unit or the like, and supplies power to each unit of teeth surface stain removing apparatus 100.

Information storage unit 420 previously stores a block information table and a control rule table. The block information table is a table that defines to which blocks each of the color-tone sensor units 230 and teeth surface electrode units 240 belongs. The control rule table is a table that defines how teeth surface electrode units 240 are caused to operate in accordance with the detection result of color-tone sensor unit 230.

Figure 6:
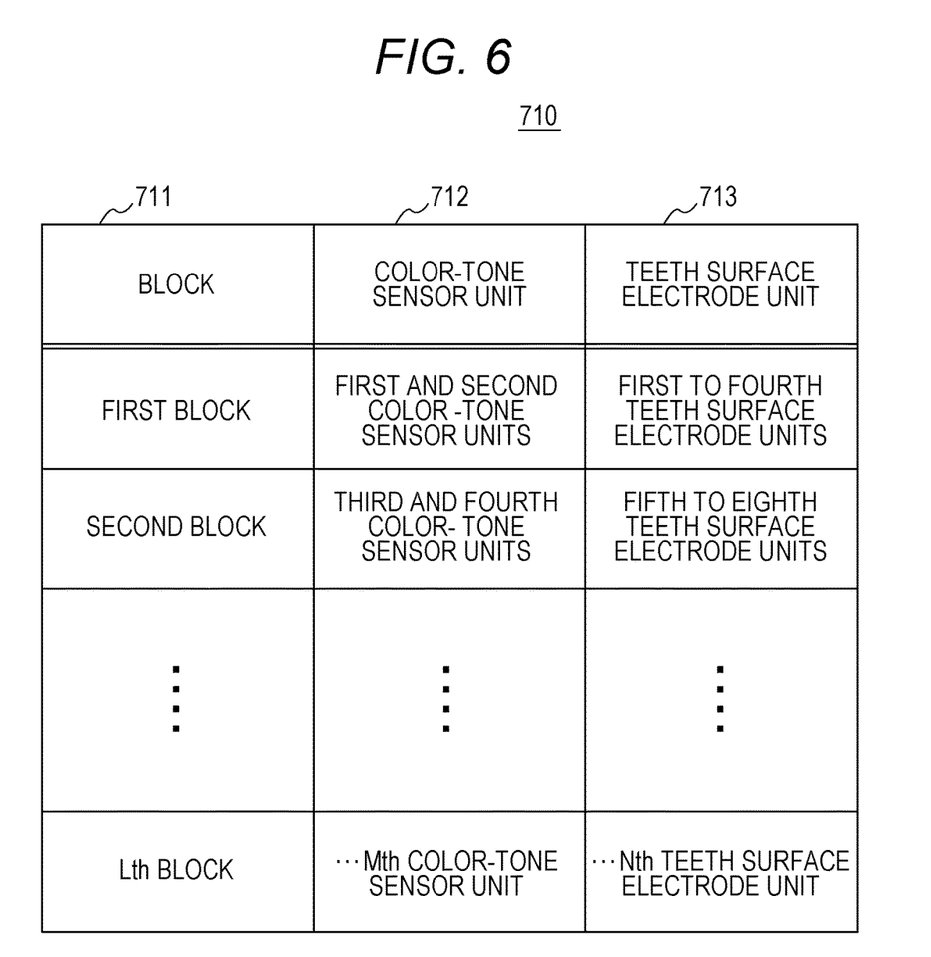
FIG. 6 shows one example of contents of a block information table according to the second exemplary embodiment.

FIG. 6 is a diagram showing one example of contents of the block information table.

As shown in FIG. 6, block information table 710 lists, in association with block identification information 711, identification information 712 of color-tone sensor units 230 disposed in the associated block. Further, block information table 710 lists, in association with block identification information 711, identification information 713 of teeth surface electrode units 240 disposed in the associated block.

For example, with first block identification information 711, identification information 712 of first and second color-tone sensor units $230_1$ and $230_2$ and identification information of first to fourth teeth surface electrode units $240_1$ to $240_4$ are associated. This is because first to fourth teeth surface electrode units $240_1$ to $240_4$ are disposed near first and second color-tone sensor units $230_1$ and $230_2$.

The region of the teeth surface where first and second color-tone sensor units $230_1$ and $230_2$ can detect color tone and the region of the teeth surface where first to fourth teeth surface electrode units $240_1$ to $240_4$ can supply charges correspond to each other. Accordingly, by controlling the operation of teeth surface electrode units 240 based on the detection result of color-tone sensor units 230 on a block-by-block basis in this manner, negative charges can be supplied at the intensity corresponding to the required degree of the stain removal process at each part.

Figure 7:
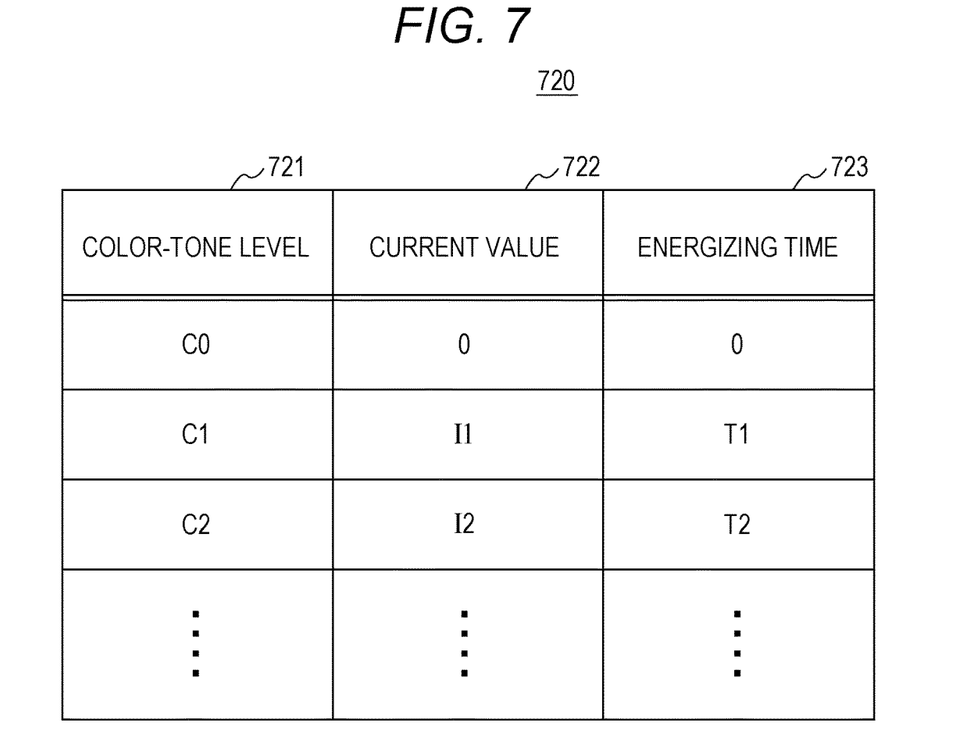
FIG. 7 shows one example of contents of a control rule table according to the second exemplary embodiment.

FIG. 7 is a diagram showing one example of contents of the control rule table.

As shown in FIG. 7, control rule table 720 lists, in association with the levels of values detected by color-tone sensor units 230 (hereinafter referred to as the "color-tone levels") 721, current values 722 corresponding to charges supplied by teeth surface electrode units 240 to the teeth surface per unit area. Further, control rule table 720 lists, in association with the color-tone levels, energizing time 723 corresponding to the current supply time of teeth surface electrode units 240.

Color-tone level 721 is, for example, the level of darkness of color of teeth. That is, color-tone level 721 is the darkness level of a stain color. For example, color-tone level 721 "C0" corresponds to the color of the teeth surface with no stains, whereas color-tone level 721 "C1" corresponds to the color of the teeth surface with slight amount of stains. With color-tone level 721 corresponding to a darker color, higher current value 722 or longer energizing time 723 is associated.

To current values 722 and energizing time 723, for example on the premise that all the blocks are substantially equal to one another in the area and the arrangement density of color-tone sensor units 230 and teeth surface electrode units 240, appropriate values are set based on experiments or empirical rules. In particular, each current value 722 is a value at which the stain removing effect can be attained without unnecessarily irritating the human body. For example, the value may be 10 µA to 300 µA per 1 $cm^2$ of each of the teeth surface and the skin with the first sheet device 200 and the second sheet device 300, respectively.

The charge supplying unit shown in FIG. 5 is connected to each of first to Mth color-tone sensor units $230_1$ to $230_M$ via a signal line (not shown) embedded in first cable 510 and first sheet device 200.

That is, charge supplying unit 430 can output a control signal to each of color-tone sensor units 230 to control the operation of color-tone sensor units 230, and can receive a detection value output from each of color-tone sensor units 230.

Further, charge supplying unit 430 is connected to each of first to Nth teeth surface electrode units $240_1$ to $240_N$ via the signal line (not shown) embedded in first cable 510 and first sheet device 200. Further, the charge supplying unit is connected to skin electrode unit 310 via a signal line (not shown) embedded in second cable 520 and second sheet device 300.

Charge supplying unit 430 boosts the output voltage of power supply unit 410 and applies the voltage across teeth surface electrode units 240 and skin electrode unit 310, and controls current flowing through the body of the user via the electrodes.

More specifically, charge supplying unit 430 determines the operation of each teeth surface electrode unit 240 based on the detection value of color-tone sensor unit 230, for each block of first sheet device 200. Charge supplying unit 430 makes such a determination by referring to block information table 710 (see FIG. 6) and control rule table 720 (see FIG. 7). Then, charge supplying unit 430 supplies charges to each teeth surface electrode unit 240 based on the determined content.

Note that, it is difficult to simultaneously apply different voltages to a plurality of teeth surface electrode units 240. Accordingly, charge supplying unit 430 groups the blocks to which identical current value and energizing time are determined. Then, when there are a plurality of groups, charge supplying unit 430 applies power to the plurality of groups time-divisionally.

Further, the structure for controlling current flowing from teeth surface electrode units 240 to skin electrode unit 310 via the body to attain a desired value may be realized by, for example, a circuit using a voltage booster circuit and a current limiting circuit, which is disclosed in Patent Literature 6. Each teeth surface electrode unit 240 includes a circuit structure for individually controlling current, at least for each block.

Note that, although not shown, control unit 400 includes, for example, a CPU (central processing unit), a storage medium such as ROM (read only memory) storing a control program, and working memory such as RAM (random access memory). In this case, the functions of the units of the control unit 400 are realized by the CPU executing the control program.

Further, although not shown, control unit 400 includes a manipulation unit such as a key switch. The manipulation unit accepts various manipulations from the user, including a manipulation for starting current supply to the teeth surface.

With the structure as described above, teeth surface stain removing apparatus 100 can perform stain removal through use of current, just by having first sheet device 200 attached to teeth and second sheet device 300 attached to the skin, starting operation.

Operation of Teeth Surface Stain Removing Apparatus

Next, a description will be given of the operation of teeth surface stain removing apparatus 100.

Figure 8:
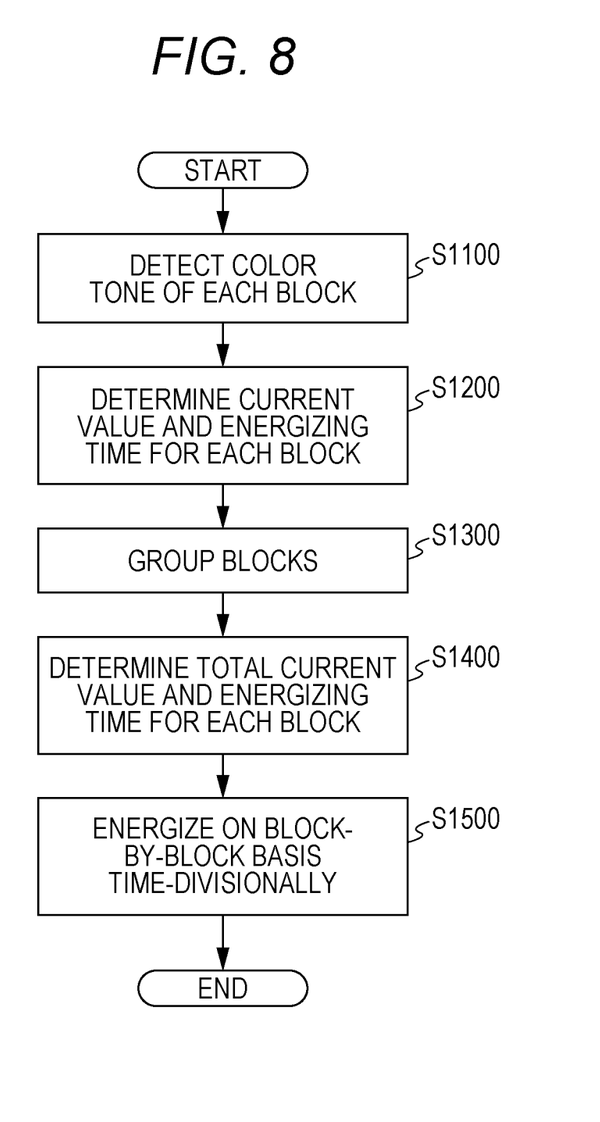
FIG. 8 is a flowchart showing one example of the operation of the teeth surface stain removing apparatus according to the second exemplary embodiment.

FIG. 8 is a flowchart showing an example of the operation of teeth surface stain removing apparatus 100.

Teeth surface stain removing apparatus 100 starts the following processes, for example when a manipulation of instructing to start operation is made by the user, in the state where first sheet device 200 and second sheet device 300 are attached to the anterior teeth portion and skin of the user, respectively.

In Step S1100, first to Mth color-tone sensor units $230_1$ to $230_M$ each detect the color tone of the nearby teeth surface, and output the detection result to charge supplying unit 430.

In Step S1200, charge supplying unit 430 acquires the average value, for each block, of the detection results from a plurality of color-tone sensor units 230 belonging to the block (hereinafter referred to as the "block detection value"). Charge supplying unit 430 refers to control rule table 720 (see FIG. 7), and determines, for each block, the current value and energizing time per unit area corresponding to the color-tone level represented by the block detection value, as the control content applied to the block. Note that, the average value of the detection results is used in order to obtain data having higher reliability.

In Step S1300, charge supplying unit 430 groups blocks to which identical current value and energizing time are determined.

Note that, when the current values are grouped into a plurality of levels, charge supplying unit 430 may treat the current values belonging to an identical level as an identical current value. Similarly, when the energizing times are grouped into a plurality of levels, charge supplying unit 430 may treat energizing times belonging to an identical level as an identical energizing time.

Further, when the color tone of the teeth surface is identical, the current value and the energizing time also become identical. Accordingly, charge supplying unit 430 may group the blocks based on the color-tone level of the teeth surface.

In Step S1400, charge supplying unit 430 determines, for each group, a total current value that should be supplied at the blocks belonging to the group, and an energizing time for the total current value. For example, the total current value is a value obtained by multiplying a current value by the total area of the blocks belonging to the group.

Then, in Step S1500, charge supplying unit 430 switches the groups in turn, and supplies negative charges to teeth surface electrode units 240 belonging to the group such that the determined total current value is attained. Then, charge supplying unit 430 continues the supply of charges during the determined energizing time using a timer (not shown) or the like. When the energizing time ends, charge supplying unit 430 transits to energize the next group. That is, charge supplying unit 430 performs energization time-divisionally on a group-by-group basis, such that the determined current value and energizing time are realized.

By such an operation, teeth surface stain removing apparatus 100 can perform the stain removal process at the intensity suitable for each part of teeth even when the extent of staining is different part-by-part. Accordingly, the stain removal can be effectively performed while suppressing the power consumption to a minimum. Note that, it is preferable that the teeth surface is wiped with absorbent cotton or the like quickly after use of teeth surface stain removing apparatus 100.

Effect of Teeth Surface Stain Removing Apparatus

As described above, teeth surface stain removing apparatus 100 according to the present exemplary embodiment includes first sheet device 200 in which teeth surface electrode units 240 that discharge negative charges and adsorptive member 250 that adsorbs stains are disposed. Teeth surface stain removing apparatus 100 according to the present exemplary embodiment includes second sheet device 300 in which skin electrode unit 310 that discharges positive charges is disposed.

Thus, teeth surface stain removing apparatus 100 can remove stains through use of current, just by having first sheet device 200 attached to teeth and second sheet device 300 attached to skin, and starting operation. That is, since teeth surface stain removing apparatus 100 does not particularly require brushing of teeth, effective stain removal through use of current can be performed more easily than the conventional technique.

Further, with teeth surface stain removing apparatus 100, since first sheet device 200 can be replaced upon use, stains can be removed in the state where hygiene of the oral cavity is maintained.

Still further, since teeth surface stain removing apparatus 100 according to the present exemplary embodiment carries out the stain removal process without the necessity of using the hands, teeth surface stain removing apparatus 100 can be used by the user while the user is performing other works or operations.

Still further, teeth surface stain removing apparatus 100 according to the present exemplary embodiment detects the color tone at each part of the teeth surface, and controls current supplied to each part.

Thus, even in the case where the color of the teeth surface varies by a tooth or by part of a tooth, i.e., where staining of teeth varies, the stain removal process can be performed for the entire anterior teeth portion proportionally. That is, teeth surface stain removing apparatus 100 according to the present exemplary embodiment can effectively perform the stain removal process on the teeth surface.

Other Example of Stain Removal Operation

Note that, charge supplying unit 430 may set one of the current value and the energizing time to a fixed value, and may vary just the other according to the color tone of the teeth surface. Alternatively, charge supplying unit 430 may determine, for each block, whether or not to energize. Further, charge supplying unit 430 periodically energize teeth surface electrode units 240, and control the energizing period or the duty cycle in accordance with the detection result of corresponding color-tone sensor units 230.

Further, charge supplying unit 430 may supply charges to the entire teeth surface, at the identical current value and energizing time. In this case, for example, charge supplying unit 430 determines the current value and energizing time of first to Nth teeth surface electrode units $240_1$ to $240_N$ based on the average value of the color tones detected by first to Mth color-tone sensor units $230_1$ to $230_M$. In this case, charge supplying unit 430 determines the current values of teeth surface electrode units 240 such that current of about 0.1 mA to 1 mA at 10 V to 15 V flows through the teeth surface as a whole. Further, in this case, charge supplying unit 430 may determine the current value not for each teeth surface electrode unit 240 but for the entire first to Nth teeth surface electrode units $240_1$ to $240_N$, and exert control regarding the whole first to Nth teeth surface electrode units $240_1$ to $240_N$ as one electrode.

Other Example of Adsorptive Member

Further, the adsorptive member may be liquid gel or a gel sheet which can be easily removed from sheet member 220. In this case, solely the adsorptive member may be disposable. That is, first sheet device 200 is not necessarily a disposable member, and is not required to include connection unit 210 to which first cable 510 can be disconnectably attached. Note that, in the case where the a liquid gel adsorptive member is employed, after the current supply and the removal of first sheet device 200 from the teeth surface, the adsorptive member must be removed from the teeth surface by being wiped off, for example.

Further, the adsorptive member desirably contains a substance promoting removal of stains, for example stain removing molecules such as polyphosphoric acid, phytic acid or the like (for example, see Patent Literature 2) or a stain decomposing enzyme (for example, see Patent Literature 7). Further, the adsorptive member may contain various substances for improving the state of the teeth surface, for example a substance reinforcing the teeth such as fluorine, a teeth bleaching substance such as hydrogen peroxide.

Other Example of First Sheet Device

Note that, first sheet device 200 may be smaller or greater than the size shown in FIG. 3. Further, teeth surface stain removing apparatus 100 may include first sheet device 200 for being attached to the upper anterior teeth portion and first sheet device 200 for being attached to the lower anterior teeth portion.

Further, first sheet device 200 may be molded using the impression of the user into a shape conforming to the teeth surface of the user. In this case, adhesion between the teeth surface and first sheet device 200 can be improved, and stains can be removed more effectively.

Still further, first sheet device 200 may have a mouthpiece-like shape covering the dental arch along its outer shape.

Still further, first sheet device 200 may not necessarily have a structure closely attached to the teeth by itself. For example, teeth surface stain removing apparatus 100 may be used with a mouthpiece-like member covering the dental arch along its outer shape. In this case, first sheet device 200 is disposed as being interposed between the mouthpiece-like member and the teeth surface.

Teeth surface stain removing apparatus 100 in the structure covering the teeth by the mouthpiece-like shape is particularly suitable for removing stains on the rear side of the teeth or on the occlusal surfaces.

Further, light emitting elements 231 of color-tone sensor units 230 are not essential. For example, a common light source emitting white-color light may be disposed at control unit 400 or the like, and the white-color light may be distributed to the blocks via optical fibers.

Other Example of Second Sheet Device

Further, second sheet device 300 may be attached to the skin of a body site other than the neck. Further, second sheet device 300 is not necessarily sheet-like, and should have shape and structure that can bring skin electrode unit 310 into contact with the skin by a relatively great area. For example, a grip-like member having an electrode surface disposed at its surface can be employed in place of second sheet device 300 according to the present exemplary embodiment.

Other Example of Control Unit

Further, control unit 400 may have a shape that can be attached to the head, an earlobe, or the neck, for example. Still further, control unit 400 may include a strap to be worn over the neck. Alternatively, control unit 400 may be structured to be used as being put in the oral cavity. For example, control unit 400 may be integrally formed with first sheet device 200.

Further, part or all of the functions of control unit 400 may be disposed on an apparatus having other main function, such as a mobile phone. Still further, part or all of the functions of control unit 400 may be disposed on a server on a network. That is, part of the functions of teeth surface stain removing apparatus 100 may be subjected to cloud migration. In this case, the apparatus unit including charge supplying unit 430 must include at least a communication unit, for transmitting data of the color-tone level of the teeth surface to the server and acquiring a current value and an energizing time to be applied to each block.

Further, teeth surface stain removing apparatus 100 may include, for each block, charge supplying unit 430 that operates solely for the block, and skin electrode unit 310 that solely corresponds to the block.

SUMMARY OF PRESENT DISCLOSURE

The teeth surface stain removing apparatus of the present disclosure is a teeth surface stain removing apparatus removing stains on a teeth surface, the apparatus including: a sheet member capable of being closely attached to the teeth surface via an adsorptive member adsorbing the stains; a teeth surface electrode unit disposed at a part of the sheet member, the part being closely attached to the teeth surface; and a charge supplying unit supplying negative charges to the teeth surface electrode unit in a state where the sheet member is closely attached to the teeth surface.

Note that, the teeth surface stain removing apparatus may include the adsorptive member.

Further, the teeth surface stain removing apparatus may include a skin electrode unit disposed at a part closely attached to a body site other than the teeth surface, wherein the charge supplying unit may apply voltage across the teeth surface electrode unit and the skin electrode unit, and may supply the negative charges from the teeth surface electrode unit to the teeth surface.

Still further, in the teeth surface stain removing apparatus, the adsorptive member may be a sheet-like electrical conductive material capable of being separated from the sheet member.

Still further, in the teeth surface stain removing apparatus, the charge supplying unit may control a magnitude of current supplied to the teeth surface per unit area via the teeth surface electrode unit.

Still further, the teeth surface stain removing apparatus may further include a connection unit that disconnectably connects between the sheet member and the charge supplying unit, wherein the sheet member carries the adsorptive member on a side closely attached to the teeth surface.

Still further, the teeth surface stain removing apparatus may further include a color-tone sensor that detects a color-tone of the teeth surface near the teeth surface electrode unit in a state where the sheet member is closely attached to the teeth surface, wherein the charge supplying unit controls the magnitude of the current based on the detected color tone.

Still further, the teeth surface stain removing apparatus may further include a light emitting element that illuminates the teeth surface near the color-tone sensor in a state where the sheet member is closely attached to the teeth surface.

Still further, in the teeth surface stain removing apparatus, the teeth surface electrode unit and the color-tone sensor may be provided at each of a plurality of divided regions obtained by dividing a surface of the sheet member on a side closely attached to the teeth surface, and the charge supplying unit may control at least one of turning ON/OFF supply of the current, and the magnitude of supplied current for each of the divided regions.

Still further, in the teeth surface stain removing apparatus, the charge supplying unit may supply negative charges time-divisionally to each of the plurality of divided regions.

A teeth surface stain removing method of the present disclosure is a teeth surface stain removing method for removing stains on a teeth surface, the method including: determining a magnitude of current supplied to a teeth surface electrode unit disposed at a part of a sheet member capable of being closely attached to the teeth surface via an adsorptive member adsorbing the stains, the part of the sheet member being closely attached to the teeth surface; and supplying the current of the determined magnitude to the teeth surface electrode unit in a state where the sheet member is closely attached to the teeth surface.

The present disclosure is useful as teeth surface stain removing apparatus and teeth surface stain removing method which make it possible to remove stains more easily.

What is claimed is:

1. A teeth surface stain removing apparatus comprising:

a first sheet member attachable to a teeth surface via an adsorptive member, the adsorptive member being capable of adsorbing stains;

a teeth surface electrode disposed at a first portion of the first sheet member, the first portion being attachable to the teeth surface;

a charge supplier that supplies negative charges to the teeth surface electrode when the first sheet member is attached to the teeth surface; and a color-tone sensor that detects a color-tone of the teeth surface located within a range from the teeth surface electrode when the first sheet member is attached to the teeth surface, wherein the charge supplier controls a magnitude of a current for supplying the negative charges to the teeth surface, based on the detected color-tone;

wherein the color-tone sensor comprises a plurality of color-tone sensors, the teeth surface electrode comprises a plurality of teeth surface electrodes, a first surface of the first sheet member is divided into a plurality of divided regions, each divided region including one of the plurality of color-tone sensors and one of the plurality of teeth surface electrodes, the first surface being structured to face the teeth surface when the first sheet member is attached to the teeth surface, the divided regions are grouped into at least two groups based on the color-tones detected by the plurality of color-tone sensors, the charge supplier supplies the negative charges time-divisionally to each of the at least two groups, and the magnitude of the current is determined for each divided region based on the detected color-tone of the divided region, the divided regions are grouped such that:

when the magnitudes of the current determined for different divided regions are identical, the different divided regions are grouped into a same group, and when the magnitudes of the current determined for different divided regions are different, the different divided regions are grouped into separate groups.

2. The teeth surface stain removing apparatus according to claim 1, further comprising the adsorptive member.

3. The teeth surface stain removing apparatus according to claim 2, further comprising:

a second sheet member attachable to a body surface other than the teeth surface; and a skin electrode disposed at a second portion of the second sheet member, the second portion being attachable to the body surface other than the teeth surface, wherein the charge supplier applies voltage between the teeth surface electrode and the skin electrode, and supplies the negative charges to the teeth surface electrode toward the teeth surface.

4. The teeth surface stain removing apparatus according to claim 3, wherein the adsorptive member is an electrically conductive material separatable from the first sheet member.

5. The teeth surface stain removing apparatus according to claim 4, wherein the charge supplier controls a magnitude of current supplied to the teeth surface per unit area via the teeth surface electrode.

6. The teeth surface stain removing apparatus according to claim 5, further comprising a connector that disconnectably connects the first sheet member to the charge supplier, wherein the adsorptive member is provided on a first surface of the first sheet member, the first surface being structured to face the teeth surface when the first sheet member is attached to the teeth surface.

7. The teeth surface stain removing apparatus according to claim 2, wherein the color-tone sensor and the teeth surface electrode are provided in the adsorptive member, and a light receiving surface of the color-tone sensor is spaced from the teeth surface, when the adsorptive member contacts the teeth surface.

8. The teeth surface stain removing apparatus according to claim 1, further comprising a light emitting element that illuminates at least part of the teeth surface when the first sheet member is attached to the teeth surface.

9. The teeth surface stain removing apparatus according to claim 8, wherein the teeth surface electrode and the color-tone sensor are provided at each of a plurality of divided regions provided on a first surface of the first sheet member, the first surface being structured to face the teeth surface when the first sheet member is attached to the teeth surface, and the charge supplier controls at least one of turning ON/OFF supply of the current, and the magnitude of supplied current for each of the divided regions.

10. The teeth surface stain removing apparatus according to claim 9, wherein the charge supplier supplies the negative charges time-divisionally to each of the plurality of divided regions.

11. A teeth surface stain removing apparatus comprising:

a first sheet member attachable to a teeth surface via an adsorptive member, the adsorptive member being capable of adsorbing stains;

a teeth surface electrode disposed at a first portion of the first sheet member, the first portion being attachable to the teeth surface;

a charge supplier that supplies negative charges to the teeth surface electrode when the first sheet member is attached to the teeth surface; and a color-tone sensor that detects a color-tone of the teeth surface located within a range from the teeth surface electrode when the first sheet member is attached to the teeth surface, wherein the charge supplier controls a magnitude of a current for supplying the negative charges to the teeth surface, based on the detected color-tone, the color tone sensor comprises a plurality of color-tone sensors, the teeth surface electrode comprises a plurality of teeth surface electrodes, a first surface of the first sheet member is divided into a plurality of divided regions, each divided region including one of the plurality of color-tone sensors and one of the plurality of teeth surface electrodes, the first surface being structured to face the teeth surface when the first sheet member is attached to the teeth surface, the divided regions are grouped into at least two groups based on the color-tones detected by the plurality of color-tone sensors, the charge supplier supplies the negative charges time-divisionally to each of the at least two groups, and the color-tones detected by the plurality of color-tone sensors are divided into a plurality of color-tone levels, the divided regions are grouped such that:

when the color-tone levels in different divided regions are identical, the different divided regions are grouped into a same group, and when the color-tone levels in different divided regions are different, the different divided regions are grouped into separate groups.

12. The teeth surface stain removing apparatus according to claim 11, further comprising the adsorptive member.

13. The teeth surface stain removing apparatus according to claim 12, wherein the color-tone sensor and the teeth surface electrode are provided in the adsorptive member, and a light receiving surface of the color-tone sensor is spaced from the teeth surface, when the adsorptive member contacts the teeth surface.

14. The teeth surface stain removing apparatus according to claim 12, further comprising:

a second sheet member attachable to a body surface other than the teeth surface; and a skin electrode disposed at a second portion of the second sheet member, the second portion being attachable to the body surface other than the teeth surface, wherein the charge supplier applies voltage between the teeth surface electrode and the skin electrode, and supplies the negative charges to the teeth surface electrode toward the teeth surface.

15. The teeth surface stain removing apparatus according to claim 14, wherein the adsorptive member is an electrically conductive material separatable from the first sheet member.

16. The teeth surface stain removing apparatus according to claim 15, wherein the charge supplier controls a magnitude of current supplied to the teeth surface per unit area via the teeth surface electrode.

17. The teeth surface stain removing apparatus according to claim 16, further comprising a connector that disconnectably connects the first sheet member to the charge supplier, wherein the adsorptive member is provided on a first surface of the first sheet member, the first surface being structured to face the teeth surface when the first sheet member is attached to the teeth surface.

18. The teeth surface stain removing apparatus according to claim 11, further comprising a light emitting element that illuminates at least part of the teeth surface when the first sheet member is attached to the teeth surface.

19. The teeth surface stain removing apparatus according to claim 18, wherein the teeth surface electrode and the color-tone sensor are provided at each of a plurality of divided regions provided on a first surface of the first sheet member, the first surface being structured to face the teeth surface when the first sheet member is attached to the teeth surface, and the charge supplier controls at least one of turning ON/OFF supply of the current and the magnitude of supplied current for each of the divided regions.

20. The teeth surface stain removing apparatus according to claim 19, wherein the charge supplier supplies the negative charges time-divisionally to each of the plurality of divided regions.

* * * * *